US00PP30566P3

(12) United States Plant Patent
van Langen

(10) Patent No.: US PP30,566 P3
(45) Date of Patent: Jun. 11, 2019

(54) ***ECHEVERIA* PLANT NAMED 'TSAECH1704'**

(50) Latin Name: ***Echeveria* hybrid**
Varietal Denomination: TSAECH1704

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 15/932,648

(22) Filed: Mar. 30, 2018

(65) Prior Publication Data

US 2018/0352712 P1 Dec. 6, 2018

(30) Foreign Application Priority Data

May 30, 2017 (QZ) ..... PBR 2017/1236

(51) Int. Cl.
*A01H 5/12* (2018.01)
*A01H 6/32* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373, 263.1
CPC ... A01H 5/12; A01H 5/00; A01H 5/02; A01H 6/32; A01H 6/00
See application file for complete search history.

*Primary Examiner* — June Hwu
(74) *Attorney, Agent, or Firm* — Samuel R. McCoy, Jr.

(57) ABSTRACT

A new and distinct *Echeveria* hybrid plant named 'TSAECH1704' which is characterized by an abundance of succulent foliage with an upright attitude, arranged in basal rosette, moderately to strongly glaucous foliage with epicuticular wax covering the upper and lower leaf surfaces, foliage colored light greyed-green on the upper leaf surface and between blue-green and greyed-green on the lower leaf surface, as well as the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'TSAECH1704'.

CROSS REFERENCE TO RELATED APPLICATIONS

This application claims priority to the Community Plant Variety Rights application number 2017/1236, filed May 30, 2017, which is herein incorporated by reference.

BACKGROUND OF THE INVENTION

Parentage: 'TSAECH1704' is an interspecific hybrid seedling selection resulting from the controlled pollination of an unnamed *Echeveria lilacina* x *Echeveria gigantea* hybrid plant (not patented), the seed parent, with an unnamed *Echeveria pulidonis* plant (not patented), the pollen parent. The crossing was made by the inventor in the summer of 2013 at a commercial greenhouse in Heerhugowaard, the Netherlands. In the summer of 2014, one seedling was observed which exhibited unique growth and foliage characteristics. The seedling was isolated for further evaluation in order to confirm the distinctness and stability of the characteristics first observed. Upon confirmation of distinctness and stability, 'TSAECH1704' was selected for commercialization in the summer of 2015.

Asexual Reproduction: Asexual reproduction of the new cultivar 'TSAECH1704', by way of rooting leaf cuttings, was first initiated in the summer of 2016 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1704' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1704'. These characteristics in combination distinguish 'TSAECH1704' as a new and distinct *Echeveria* hybrid cultivar:

1. 'TSAECH1704' exhibits an abundance of spatulate to obovate succulent foliage with an upright attitude, arranged in basal rosette; and
2. 'TSAECH1704' exhibits moderately to strongly glaucous foliage with epicuticular wax covering the upper and lower leaf surfaces; and
3. 'TSAECH1704' exhibits foliage colored light greyed-green on the upper leaf surface and between blue-green and greyed-green on the lower leaf surface.

BOTANICAL DESCRIPTION OF THE PLANT

Figure 1:
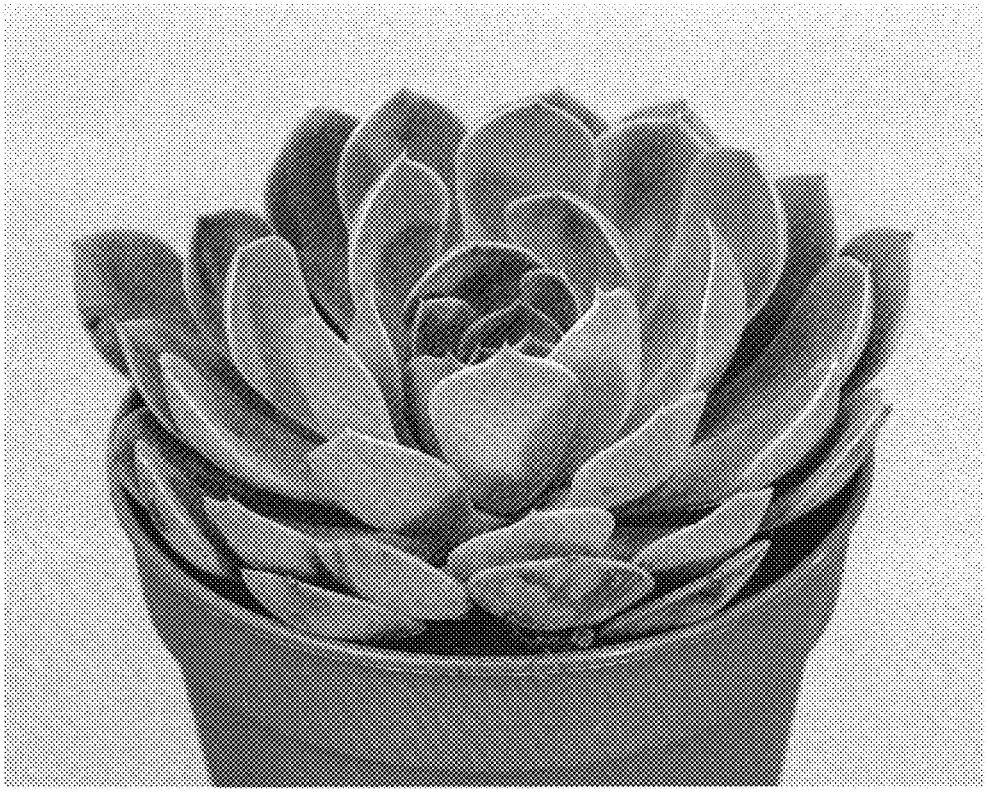
FIG. 1 illustrates, as nearly true as it is reasonably possible to make the same in color photographs of this type, an exemplary plant of 'TSAECH1704' grown in a commercial greenhouse in Heerhugowaard, the Netherlands. This plant is approximately 6 months old, shown planted in a 12 cm container.
Figure 2:
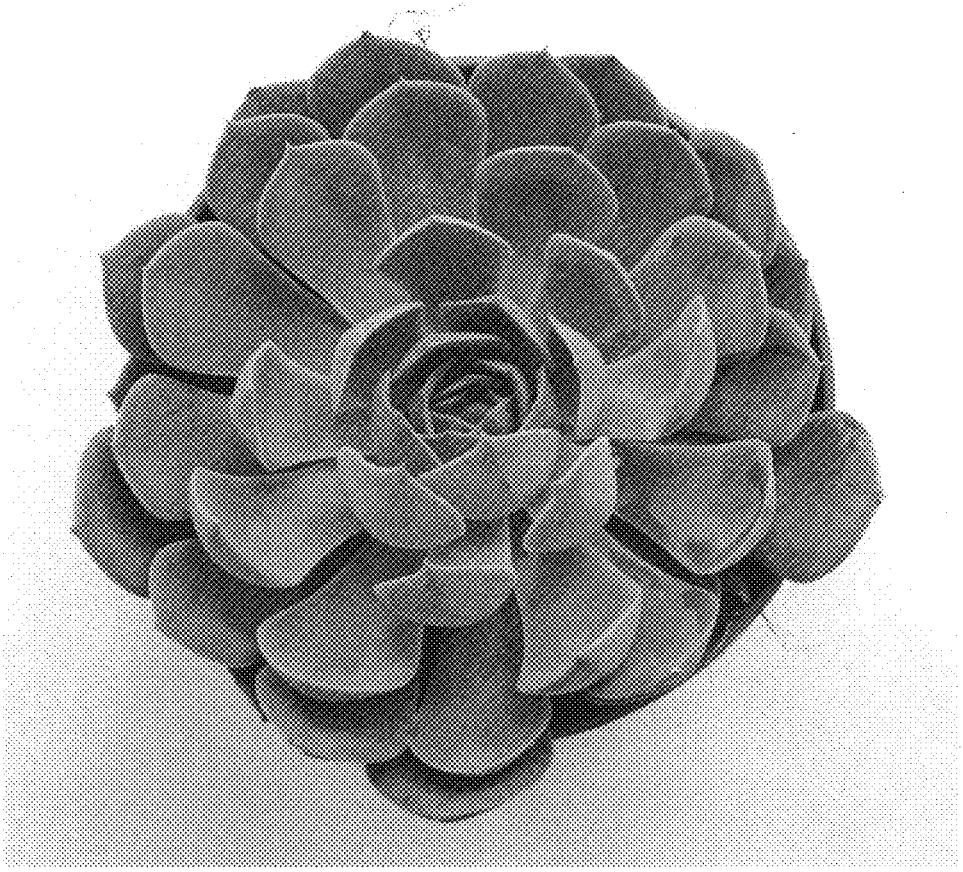
FIG. 2 illustrates, as nearly true as it is reasonably possible to make the same in color photographs of this type, the typical foliage arrangement of 'TSAECH1704.
Figure 3:
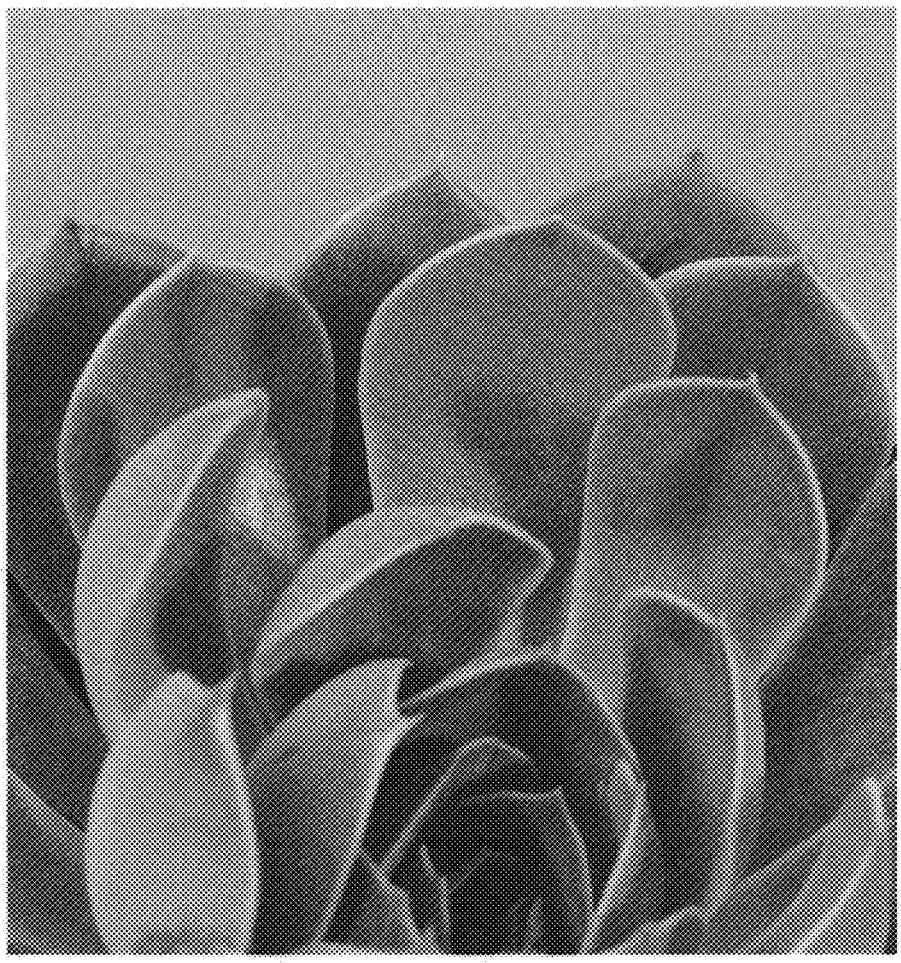
FIG. 3 illustrates, as nearly true as it is reasonably possible to make the same in color photographs of this type, the adaxial surface of the mature foliage 'TSAECH1704'.
Figure 4:
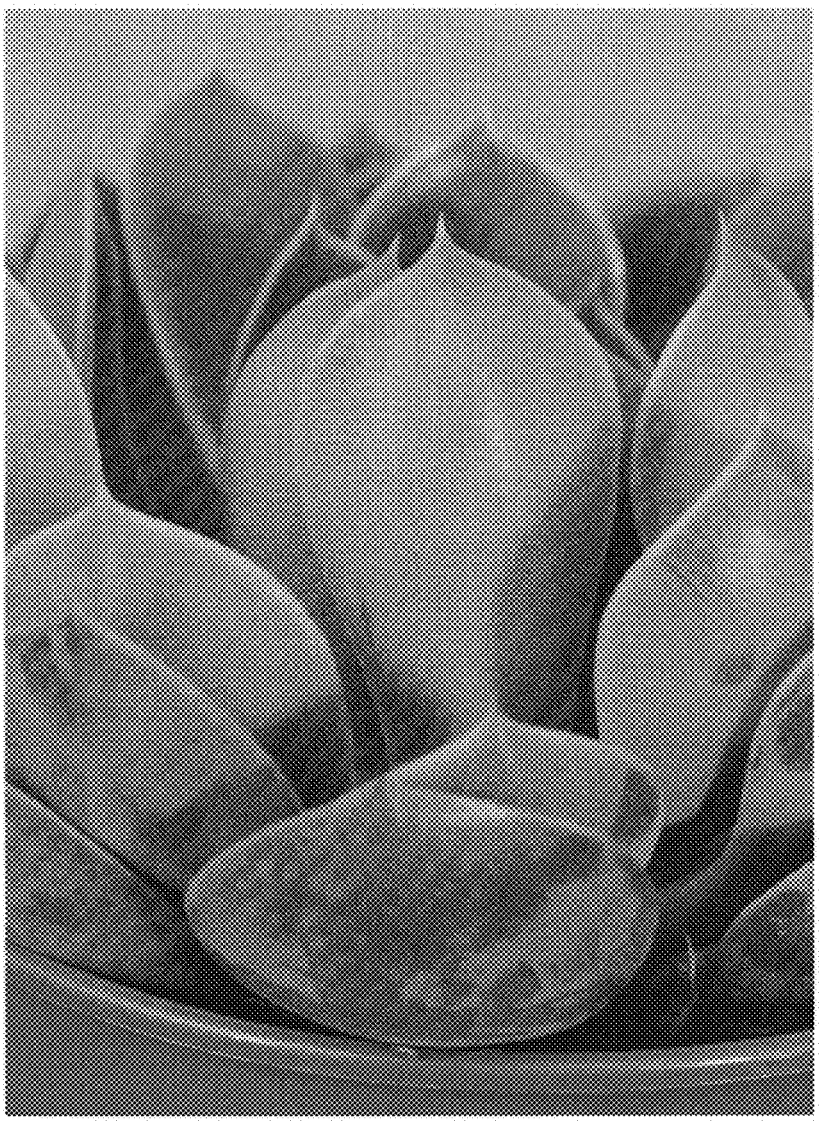
FIG. 4 illustrates, as nearly true as it is reasonably possible to make the same in color photographs of this type, the abaxial surface of the mature foliage 'TSAECH1704'.

The following observations and measurements made in January of 2018 describe averages from a sample set of six specimens of 6 months old 'TSAECH1704' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1704' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1704' and comparisons with the parent plants and closest known comparator are provided below.

Plant description:

*Growth habit.*—Succulent perennial with foliage growing in a non-branched basal rosette.

*Plant shape.*—Flattened globular.

*Height from soil level to top of foliar plane.*—6.1 cm.

*Plant spread.*—Average of 13.1 cm.

*Growth rate.*—Moderate.

*Plant vigor.*—Moderate.

*Propagation.*—Type — Leaf cuttings. Time to initiate rooting — Approximately 21 days at 18 degrees Celsius. Crop time — Approximately 35 weeks to produce a marketable plant in a 12 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 54 leaves per rosette.

*Shape.*—Thick, succulent leaves which are spatulate to obovate.

*Dimensions.*—6.3 cm long, 2.5 cm wide, and 0.5 cm thick, on average.

*Aspect.*—Moderately concave and slightly to moderately curved upward.

*Attitude.*—Younger foliage near the center of the rosette is very upright; foliage becoming progressively more relaxed towards the outer whorl of the rosette yet still generally upright; average angle of 50 degrees from horizontal.

*Apex.*—Apiculate.

*Base.*—Cuneate.

*Margin.*—Entire; not undulated or lobed.

*Pubescence, texture and luster of the adaxial surface.*—Glabrous, smooth, and matte; moderately to strongly glaucous.

*Pubescence, texture and luster of the abaxial surface.*—Glabrous, smooth, and matte; moderately to strongly glaucous.

*Color.*—Juvenile foliage, adaxial surface — In between yellow-green to greyed-green, nearest to RHS 148B and 191B, and fading to a lighter shade of greyed-green towards the base, nearest to RHS 194D; narrowly margined greyed-white, nearest to RHS 156C occasionally lightly suffused pink along distal margin; the epicuticular glaucous wax covering the leaf surface is greyed-green, nearest to RHS 188B. Juvenile foliage, abaxial surface — Yellow-green, nearest to RHS 148B, and fading greyed-green towards the base, nearest the RHS 193B; narrowly margined greyed-white, nearest to RHS 156C occasionally lightly suffused pink along distal margin; the epicuticular glaucous wax covering the leaf surface is colored between blue-green and greyed-green, nearest to RHS 112C and 188B. Mature foliage, adaxial surface — Greyed-green, nearest to RHS 191A, and fading lighter towards the base, nearest to RHS 193B; narrowly margined green-white, nearest to a mixture of RHS 157C and 157D occasionally lightly suffused pink along distal margin; the epicuticular glaucous wax covering the leaf surface is greyed-green, nearest to RHS 188B. Mature foliage, abaxial surface — Yellow-green, nearest to RHS 147B, and fading to greyed-green towards the base, nearest to a mixture of RHS 192A and 192B; narrowly margined green-white, nearest to a mixture of RHS 157C and 157D occasionally lightly suffused pink along distal margin; the epicuticular glaucous wax covering the leaf surface is colored between blue-green and greyed-green, nearest to RHS 112C and 188B.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1704' differ from the parent, an unnamed *Echeveria lilacina* x *E. gigantea* hybrid plant, in the following characteristics described in Table 1 below.

TABLE 1

| Characteristic | 'TSAECH1704' | Echeveria hybrid seed parent. |
|---|---|---|
| Foliage abundance. | More abundant. | Less abundant. |
| Foliage width. | Narrower than the seed parent. | Wider than 'TSAECH1704'. |
| General coloration of the foliage. | Light grey with a pink hue. | Appearing as light lilac suffused with white. |

Plants of the new cultivar 'TSAECH1704' differ from the pollen parent, an unnamed *Echeveria pulidonis* plant (not patented), in the following characteristics described in Table 2 below.

TABLE 2

| Characteristic | 'TSAECH1704' | Echeveria pulidonis pollen parent. |
|---|---|---|
| Foliage abundance. | More abundant. | Less abundant. |
| Foliage attitude. | More upright. | Less upright; i.e. more relaxed. |
| General coloration of the foliage. | Light grey with a pink hue. | Green and margined red. |

COMPARISONS WITH THE CLOSEST KNOWN COMPARATOR

Plants of the new cultivar 'TSAECH1704' differ from the closest known commercial comparator, the common form of the species *Echeveria pullox* (not patented), in the following characteristics described in Table 3 below.

TABLE 3

| Characteristic | 'TSAECH1704' | Echeveria pullox |
|---|---|---|
| Foliage width. | Narrower than Echeveria pullox. | Wider than 'TSAECH1704' |
| Foliage abundance. | More abundant. | Less abundant. |

That which is claimed is:

1. A new and distinct variety of *Echeveria* hybrid plant named 'TSAECH1704', substantially as described and illustrated herein.

* * * * *